United States Patent [19]

Bossuyt

[11] Patent Number: 4,953,400
[45] Date of Patent: Sep. 4, 1990

[54] METHOD OF MEASURING THE YARN DENSITY OF A WOVEN FABRIC OR THE STITCH DENSITY OF A KNIT FABRIC FOR READJUSTING THE PRODUCTION MACHINE IN QUESTION

[75] Inventor: Filip O. P. Bossuyt, Kortrijk, Belgium

[73] Assignee: "Wetenschappelijk en Technisch Centrum van de Belgische Textielnijverheid", afgekort tot "Centexbel", Brussels, Belgium

[21] Appl. No.: 394,270

[22] Filed: Aug. 15, 1989

Related U.S. Application Data

[63] Continuation-in-part of Ser. No. 152,364, Feb. 4, 1988, abandoned.

[30] Foreign Application Priority Data

Feb. 5, 1987 [BE] Belgium ............................ 08700088

[51] Int. Cl.[5] ...................... G01B 11/00; D03D 51/00
[52] U.S. Cl. ........................................ 73/159; 139/1 B; 139/1 D; 139/1 E; 26/70; 66/54; 356/238; 358/101
[58] Field of Search ................... 73/159, 160; 139/1 B, 139/1 D, 1 E, 309; 356/429, 430, 431, 237, 238, 242; 358/106, 107, 101; 26/70; 66/54, 55, 166

[56] References Cited

U.S. PATENT DOCUMENTS

| | | |
|---|---|---|
| 2,882,785 | 4/1959 | Biesele, Jr. |
| 4,124,300 | 11/1978 | Mead et al. ............. 356/429 |
| 4,509,076 | 4/1985 | Yoshida ................... 356/431 |
| 4,582,095 | 4/1986 | Kromholm ............... 139/1 R |
| 4,619,527 | 10/1986 | Levenberger et al. ... 356/430 |
| 4,643,230 | 2/1987 | Remmer et al. ......... 139/1 B |
| 4,648,712 | 3/1987 | Brenholdt ................ 356/429 |
| 4,665,317 | 5/1987 | Ferriere et al. ......... 356/430 |

FOREIGN PATENT DOCUMENTS

0160895 11/1985 European Pat. Off. .

*Primary Examiner*—Harvey C. Hornsby
*Assistant Examiner*—Joseph S. Machuga
*Attorney, Agent, or Firm*—Stevens, Davis, Miller & Mosher

[57] ABSTRACT

A method of measuring the yarn density of a woven fabric or the stitch density of a knitted fabric by recording a video image of the woven or knitted fabric to be examined by means of a video camera, converting the video image by an analog-to-digital converter into digital video information, storing the digital video information in a digital image memory and converting said information by a central processing unit into the yarn density or stitch density. The digital video information is converted by a digital band filter (14) with central circle frequency ($\omega_o$) into a yarn or stitch density, and that the digital band filter (14) is arranged in such a manner that it operates according to the formula:

$$Y_k = A_m \cdot X_{k-m} + A_{m-1} \cdot X_{k-m+1} \cdots + A_o X_k - B_1 \cdot Y_{k-1} - B_2 Y_{k-2} \cdots B_n Y_{k-n}$$

wherein:

$X_k$ represents a series of points of the digital information characteristic at interspace T before the digital filtering;
$Y_k$ represents the said series of points k of the filtered digital information characterisitcs via digital filtering at the same interspace T; the coefficients A and B are a function of the quality Q, the central circle frequency $\omega_o$ and the interspace T.

30 Claims, 5 Drawing Sheets

Q 1

Q 4

Q 8

METHOD OF MEASURING THE YARN DENSITY OF A WOVEN FABRIC OR THE STITCH DENSITY OF A KNIT FABRIC FOR READJUSTING THE PRODUCTION MACHINE IN QUESTION

This application in a continuation-in-part of application Ser. No. 152,364, filed Feb. 4, 1988, now abandoned.

This invention relates to a method of measuring the yarn density of a woven fabric or the stitch density of a knit fabric, for readjusting the production machine in question, such as a loom, knitting machine or tenter frame, automatically and continuously, in case of deviation from the desired density.

In the weaving industry, it is useful to know on-line the weft density of the fabrics produced: on the basis of this data, the operator can adjust the instructed weft density on the production machine as accurately as possible. Approximating this weft density has an economic importance: too high a weft density naturally results in loss of raw materials, and too low a density leads to complaints from customers. Moreover, a measurement of the weft density also permits to detect certain errors, such as beating errors.

In the knit fabric industry, the dimensional stability of the knit fabric is one of the major quality characteristics of the finished product. By measuring the stitch density during several phases of the production process, it is possible better to control the stability of the knit fabrics produced.

The measuring method commonly used is the manual count of the number of yarns over a given distance (minimum distances are specified according to the standards for different density categories). This method has the advantage that it is simple, but on the other hand it is not so accurate and time-consuming.

An alternative for the above method is to ravel out a piece of cloth with known dimensions, followed by a count of the yarns raveled out, which is highly time-consuming.

A third known method is the use of fine grids laid over the piece of textile to be analyzed. With a well-chosen grid, there is obtained a certain moirépattern, from which the density can easily be determined. This method has the advantage of being quicker and less stressful; accuracy, however, is less good.

A further drawback of this known method is that the operator, after establishing a deviation in density, always has to adjust the loom, knitting machine or tenter frame, which is a relatively slow process, so that the deviation in density is not removed as quickly as necessary. Moreover, such a process is time-consuming and insufficiently accurate.

It is an object of the present invention to remove these drawbacks and to provide a method of measuring the yarn density of a fabric or the stitch density of a knit fabric that is highly accurate and fast, and in which the measuring data corresponding with the yarn density and stitch density, is used for controlling the loom, knitting machine or tenter frame concerned.

To that end, a video image of the woven or knitted fabric is picked up by a video camera and the video image is converted in an analog-to-digital converter into digital video data, which is stored in a digital image memory for it to be digitally converted by a central processing unit into the yarn density or stitch density by means of a digital filter with a central circle frequency, said filter being arranged so that it is operated according to the formula:

$$Y_k = A_m \cdot X_{k-n} + A_{m-1} \cdot X_{k-m} \cdots + A_o X_k - B_1 \cdot Y_{k-1} B_2 Y_{k-2} \cdots - B_n Y_{k-n}$$

wherein: $X_k$ represents a series of points of the digital data characteristic at interspace T before the digital filtering; $Y_k$ represents the said series of points k of the filtered digital data characteristic after digital filtering at the same interspace T; the coefficients A, and B are a function of the quality factor Q, the central circle frequency $\omega_o$ and the interspace T.

$\omega_o$ is the central pulsation or central circle frequency of the band pass filter. equations in the filter theory can be written in the function of $\omega$ or in the function of f.

The central frequency fo of a band pass filter is the frequency at which the amplitude of the output signed is maximal (see FIG. 7).

The aim of the filter is to eliminate all unwanted signal (signals differing from the nominal yarn frequency). If e.g. the fabric has a normal density (or yarn frequency) of 15 yarns/cm, the band pass filter is adjusted to a central frequency fo=15 (corresponding to a central pulsation $\omega_o = 2\pi \times 15$).

For most of the fabrics it is enough to calculate once and for all $\omega_o$ per fabric quality and it is not necessary to recalculate $\omega_o$ during the measuring.

Only in cases of very irregular woven fabrics or in knit fabrics it can be useful to adjust $\omega_o$ from time to time during the measuring on the basis of the measured average yarn frequency. It is certainly not indicated to adjust the central frequency fo of the filter after each measuring; this would cause unstability.

Q is the quality factor of the band pass filter and a measure of the selectivity of the filter. The higher the quality factor the more selective the filter. Reference is made to FIGS. 7 and 8.

FIGS. 7 and 8 are also valid for stepped waves. In fact each form of wave stored in the memory of a computer is stepped. The smooth sinusoidal wave of FIG. 8 can be thus replaced by a stepped wave as shown in FIGS. 3 and 4. The suffix o is used to indicate that it is the central circle frequency. The equation:

$$\omega_o = 2\pi f$$

is a generally known equation of formal nature to pass from a pulsation or circle frequency $\omega$ to a frequency f. All The filtered digital data characteristic or the yarn or stitch density data obtained after digital filtering is supplied to the loom, knitting machine or tenter frame for controlling the loom, knitting machine or tenter frame in such a manner that it delivers a woven or knitted fabric whose density can be accurately maintained within certain limits. Possibly, this density data can also be supplied to a read-out unit for visualizing these data, on the basis of which the operator can see to what extent there are deviations in the woven pattern.

Advantages of the method according to the present invention are that the measurement can be easily performed automatically with a high accuracy, that human errors during counting, e.g. of the number of stitches, are excluded, and that the measurement is done much more quickly than with the manual method.

Moreover, the method allows a continuous measurement, permitting a quicker intervention in the production process, so that a constant quality of the woven or knitted fabric is obtained.

In a particular embodiment of the method according to the present invention, the central circle frequency $\omega_o$ of the digital filter is designed to be adjustable as a function of the yarn or stitch density of the fabric to be examined.

In an advantageous embodiment of the method according to the present invention this data is enhanced before the conversion of the digital video data.

Preferably, enhancing the digital video data includes at least one of the following steps: contrast expansion, elimination of redundant data from the digital video data and accentuation of relevant data in the digital video data.

The yarn or stitch frequency graph can be calculated by isolating one line from the digital video data or by calculation from the digital image information of a row or column histogram.

The present invention also relates to an apparatus that is particularly suitable for performing the method according to the present invention.

The invention accordingly relates to an apparatus for measuring the yarn density of a woven fabric or of the stitch density of a knit fabric, which is characterized in that it comprises:

a video camera arranged to record an analog video image from the woven or knitted fabric to be examined;

an analog-to-digital converter converting the analog video image into digital video data;

an image memory for storing the digital video data, and a processing unit for converting the digital video data into the yarn or stitch density by means of a digital filter having a central circle frequency.

Other features and advantages of the present invention will become apparent from the following description of a method of measuring the yarn density of a woven fabric or of the stitch density of a knit fabric according to the present invention; this description is given by way of example only and is not intended to limit the invention in any way; the reference numerals refer to the accompanying drawings, in which.

In the various figures, the same reference numerals relate to the same elements.

Figure 1:
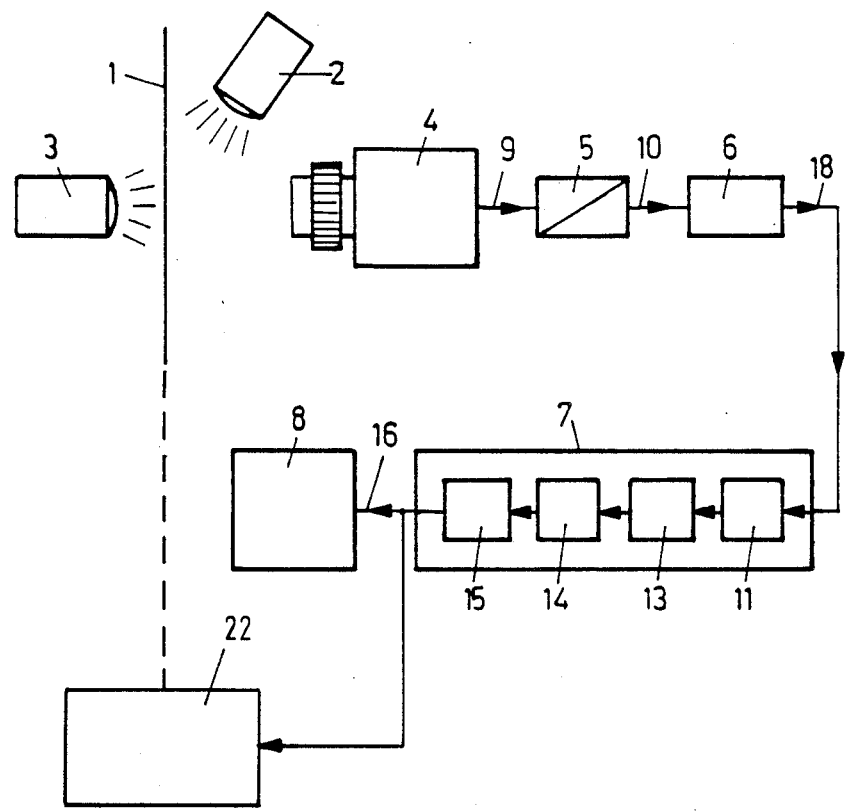
FIG. 1 is a diagrammatic representation of the apparatus for measuring the yarn or stitch density according to the present invention.

The woven or knitted fabric 1 to be examined, according to its properties and the circumstances, is exposed with incident light from a light source 2 or with light passing through it from a light source 3.

The measuring arrangement according to the present invention comprises a camera 4, which may be a CCD video camera, a fast analog-to-digital converter 5, an image memory 6, a processing unit 7, containing the means for digitally processing the image and after which the data is supplied to a display unit 8, and as control data to a production machine 22, such as a loom, knitting machine or tenter frame.

An analog video image of the woven or knitted fabric 1 is recorded by the camera 4 during the manufacture or treatment of said woven or knitted fabric by the production machine 22. The analog video image is applied through lead 9 to the fast analog-to-digital converter 5, which converts the analog video image into digital video data, consisting of a series of measuring points having a digital value. From the fast analog-to-digital converter 5 through lead 10 the digital video data is applied to, and stored in, the image memory 6. In this stage the digital video data is not yet suitable for further processing, since it still contains redundant data. This redundant data should first be removed from the digital video data, which takes place in the processing unit 7, containing an image enhancing unit 11 for enhancing the digital image or the digital video data.

To that end, the digital video data is retrieved from the image memory 6 via connection 18 and applied to the image enhancing unit 11 of the processing unit 7. Accordingly, this image enhancing unit 11 performs preparatory operations on the digital video data, such as image enhancement by e.g. contrast expansion, elimination of redundant data, accentuation of relevant data and the like.

After this step, a yarn or stitch frequency graph 12 is derived from the enhanced video data by a part 13 of the processing unit 7. This can be done in two ways:

A first way is the isolation of one line from the video image now existing in the form of digital video data.

Figure 3:
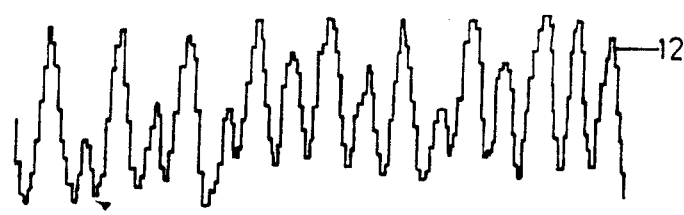
FIG. 3 is a graph of the digitalized picture points or pixels of a line recording or of a histogram before digital filtering.

By considering the brightness of each digital measuring point of a line in function of the place of that measuring point in the line, there are obtained a series of points defined as the data corresponding with the yarn or stitch frequency graph 12, which graph is shown in FIG. 3.

A second manner is the calculation of a row or column histogram. Per row or column, the intensities of all digital measuring points present in the row or column under consideration are summed. The graphic representation of all sums of intensities forms a row or column histogram that likewise has the form of the graph of FIG. 3.

The computation of the density from the data corresponding with the yarn frequency graph of FIG. 3 takes place in two stages.

The first stage comprises a pre-treatment of the graph of FIG. 3 by digital filtering, in a digital filter unit 14 of the processing unit 7. In the ideal case of a perfectly regular fabric, whether woven or knitted, the data corresponding with the yarn frequency graph 12 is a perfectly periodic signal having a constant frequency.

In a normal case, however, this signal is not perfectly periodic: various spurious and interfering frequencies are superposed on the fundamental frequency. These spurious frequencies are filtered out in the digital filter unit 14 by means of a digital band filter, a digital low-pass filter and/or a digital high-pass filter present therein.

Band filters are especially interesting, because they enable the accentuation of a specific frequency band in the signal. The central frequency of that band filter is then adjusted each time by the operator of the loom, knitting machine or tenter frame in function of the fabric being examined.

Figure 2:
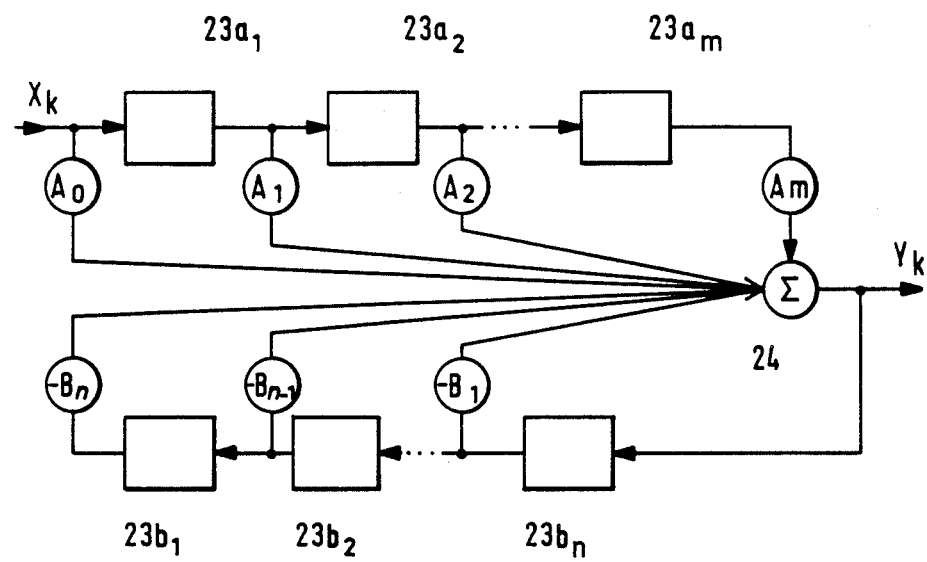
FIG. 2 is a diagram of the digital filter used in the apparatus.

FIG. 2 diagrammatically shows an embodiment of the digital filter 14 with central circle frequency $\omega_o$ of FIG. 1. This filter comprises a plurality of delay units $23a_1 \ldots a_m$ and $23b_1 \ldots b_n$, and a summing circuit 24. The manner in which these delay units are connected to the summing circuit is further shown in FIG. 2, and they jointly form a specific digital filter algorithm.

Figure 5:
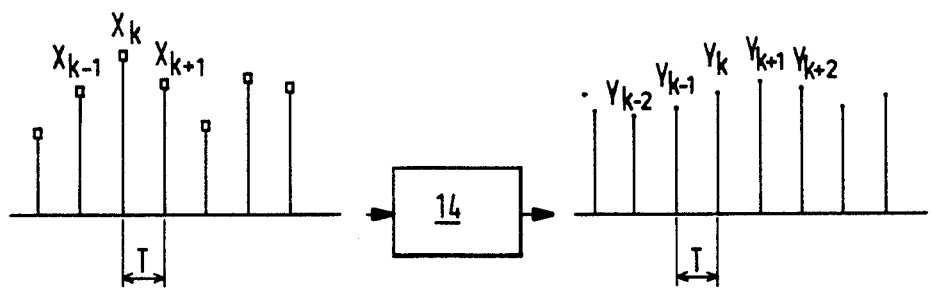
FIG. 5 is a graph of the picture points to be calculated before and after digital filtering.

The yarn or stitch frequency graph 12, see FIG. 3, supplied to the input of filter 14, consists of a row of points $X_k$ being at an interspace T from each other, see FIG. 5. These will be converted by the digital filter algorithm to a new row of points $Y_k$ at the output of filter 14.

The general form of such a filter algorithm is as follows:

$$Y_k + B_1 \cdot Y_k + B_2 \cdot Y_{k-2} \ldots + B_n \cdot Y_{k-n} = A_m \cdot X_{k-m} + A_{m-1} \cdot X_{k-m-1} \cdots = A_o \cdot X_k$$

or $$Y_k = A_m \cdot X_{k-m} + A_{m-1} \cdot KX_{k-m+1} \cdots + A_o \cdot X_{B1 \cdot k} - B_2 \cdot Y_{k-2} \ldots - B_n \cdot Y_{k-n}$$

The filter coefficients $A_o \ldots A_m$ and $B_o \ldots B_n$ define the nature of the filter and should therefore be calculated from the filter specifications.

For a classical 2nd order band filter with central circle frequency $\omega_o$ and quality factor Q, the following formula is found:

$$Y_k + B_1 \cdot Y_{k-1} + B_2 \cdot Y_{k-2} = A_o \cdot X_k + A_1 \cdot X_{k-1} + A_2 \cdot X_{k-2}$$

$$Y_k = A_2 \cdot X_{k-2} + A_1 \cdot K_{k-1} + A_o \cdot X_k - B_1 \cdot Y_{k-1} - B_2 \cdot Y_{k-2}$$

The coefficients A and B are a function of Q, $\omega_o$ and T (the distance between two successive points of the row of points) in which:

$A0 = 2\alpha$ $$A1 = -2\alpha \cdot e^{-\alpha} \left( \frac{\sin \alpha \beta}{\beta} + \cos \alpha \cdot B \right)$$

$A2 = o$
$B1 = -2^{-\alpha} \cdot \cos \alpha \beta$
$B2 = e^{-2\alpha}$ wherein $$\alpha = \frac{\omega_o T}{2Q} \quad B = \sqrt{4 Q^2 - 1}$$

A mathematic meaning of $\omega_o$ and Q is given by the transfer function of the band pass filter:

$$H(s) = \frac{\omega_o}{Q} \cdot \frac{s}{s^2 + \frac{\omega_o}{Q} + \omega_o^2}$$

(s = Laplace transform of time)

This equation is the Laplace transform of the output signal divided by the Laplace transfer of the input signal. This transfer function comprises all information with respect to the frequency reproduction of a linear system (as an analog filter). For digital filters it is necessary to pass from Laplace transforms to Z-transforms.

The coefficients A0, A1, A2 and B0, B1, B2 are obtained from the digital transfer function. This is the Z-transform of the output divided by the Z-transform of the input.

The method to pass from Laplace transforms to Z-transforms is known e.g. from "Signals and Linear Systems" from A. Gabel and A. Roberts, editor John Wiley & Sons—chapter 7 concerns the calculation of digital filters.

The calculations of the coefficients are complicated and are irrelevant to the invention. The invention concerns the use of a digital filter, operating according to a determined formula, for calculating the yarn of stitch density and so readjusting the production machine but not the calculation of said filter as such, which calculation is performed according to a known method.

The equations of Alfa and Beta are conventional: in the equation of the transformed digital transfer function D (z) the functions $\omega_o T/2Q$ and $\sqrt{4 \cdot Q^2 - 1}$ appear often. By replacing them by Alfa and Beta, the equation is simpler:

$$D(z) = 2\alpha \frac{1 - z \cdot e^{-\alpha} \cdot \left( \frac{\sin \alpha \beta}{\beta} + \cos \alpha \cdot \beta \right)}{1 - 2z \cdot e^{-\alpha} \cdot \cos (\alpha \cdot \beta) + z^2 \cdot e^{-2\alpha}}$$

From this equation A0, A1, and B0, B1 can be obtained as an equation as shown.

In the classical analog filters, filtering takes place by means of physical components (capacitor, coil). The value of these components and the manner in which they are connected determines the characteristics of the filter (cut-off frequency, band width, quality factor, high-pass or low-pass). When these characteristics are to be changed, it is necessary to intervene in the circuit arrangement. The electrical diagram or the value of one of the components thereof will have to be changed. It is not possible to render the central circle frequency $\omega_o$ controllable without, in this case too, changing the filter value.

In a digital filter, however, filtering takes place by means of mathematical operations; in other words, by an algorithm applied to a row of numbers in the memory of a computer. The characteristics of a digital filter are determined by a number of coefficients and not by physical components. The filter characteristics can thus be adjusted in a simple and fast manner; the filter is entirely software-programmable.

For filtering the yarn frequency characteristic, it is necessary to have a band filter whose central frequency is equal to the yarn frequency of the textile to be measured. This can be realized easily with the digital filtering described herein.

It is even possible to adjust the filter n the basis of the measured density, in other words to render the system "self-teaching". In a teaching phase, filtering takes place then on the basis of an estimated central circle frequency. On the basis of the measurements, this central circle frequency is then adjusted to obtain an optimally effective filtering.

Figure 9:
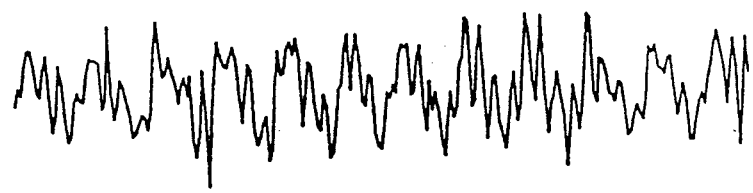
FIG. 9 shows the yarn frequency characteristic for three different values of Q.
Figure 9:
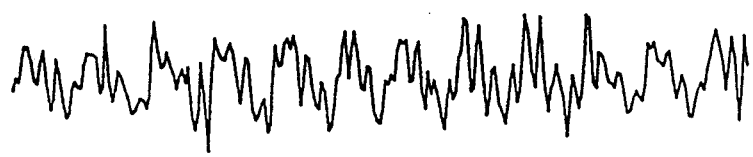
Figure 9:
Figure 9:
Figure 9:

The manner of influencing the filtering by changing Q is illustrated in FIG. 9. FIG. 9 shows a yarn frequency characteristic for three different values of Q (1,4 and 8) before filtering and after being three times filtered. It can be seen that the higher the quality factor Q, the more selective the filter. The choice of the appropriate Q is made by experimentation. Although it seems favorable to choose Q very high, this could be undesirable as a too high Q (a too selective filter) also filters out the useful information when there exists a small local deviation from nominal fabric density. Filters with a high Q also need a certain initiation time. The amplitude of the filtering signal is clearly weakened at the beginning with respect to filters with lower Q.

The choice of Q has no significant influence on the final result of the calculations, so far as, of course, one does not go beyond certain limits. The filtering width Q=1 shown in FIG. 9 is clearly insufficient as in the filtered signal high frequencies can still be observed. Filters with Q4 and Q8 are on the contrary sufficient. The results of the calculation of the density will be the same for both filters. This is due to the fact that the filtering is a linear operation; the frequencies in the signal are not modified; only the amplitude of components of no interest is weakened. The base frequency (which is equal to the yarn frequency) is not changed by the filter.

Figure 4:
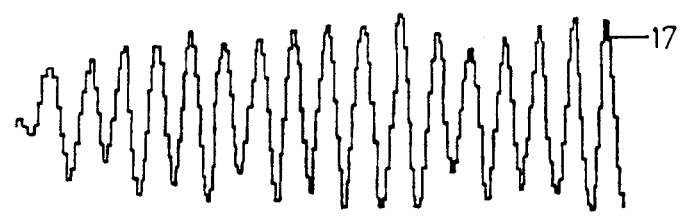
FIG. 4 is a graph of the digitalized picture points or pixels of the same line recording or histogram of FIG. 2 after digital filtering.

The second phase comprises the computation proper of the yarn density from the data filtered out from the digital filter unit 14, corresponding with the yarn or stitch frequency graph 17, shown in FIG. 4, in a computing unit 15 of the processing unit 7.

First, the average of the filtered data corresponding with the yarn or stitch frequency graph 17 is computed and detracted from the data corresponding with the graph, after which the number of whole periods N in the data corresponding with graph 17 is counted. Subsequently, the number of picture points (or pixels) $N_p$ in these N periods is counted. The yarn or stitch density is then obtained by the simple step: yarn or stitch density $= N/(N_p \times s)$ in which s is a scale factor defined by the calibration procedure to be described hereinafter.

To obtain a density measurement that is as accurate as possible (absolute density measurement), use is made of a calibration pattern that may be a separate, specific pattern for each type of fabric.

A calibration pattern consists e.g. of a metal foil on which are provided a plurality of parallel lines that are regularly interspaced. This interspace is accurately determined.

Such a calibration pattern is read out by means of the measuring arrangement shown in FIG. 1 and the frequency characteristic of this read-out calibration pattern is calculated, after which the number of whole periods $N_y$ and the number of pixels $N_y P$ are counted from this frequency characteristic. The length of one pixel, i.e. the line distance $s_y$ of the calibration pattern, can then be represented by $$s_y = N_y / N_y P$$

This $s_y$ corresponds with the above average scale factor s.

By replacing s in the above indicated expression of the yarn or stitch density by the expression indicated for $s_y$, there is obtained the absolute yarn or stitch density measurement.

Figure 6:
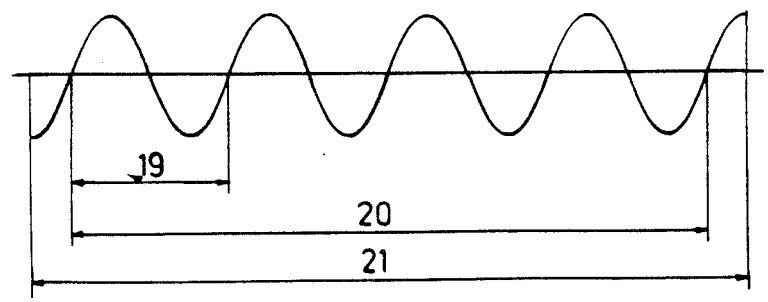
FIG. 6 is a graph of the digitalized picture points of a line recording or of a histogram of the digital filtering serving as a basis for the calculation of the yarn or stitch density.
Figure 7:
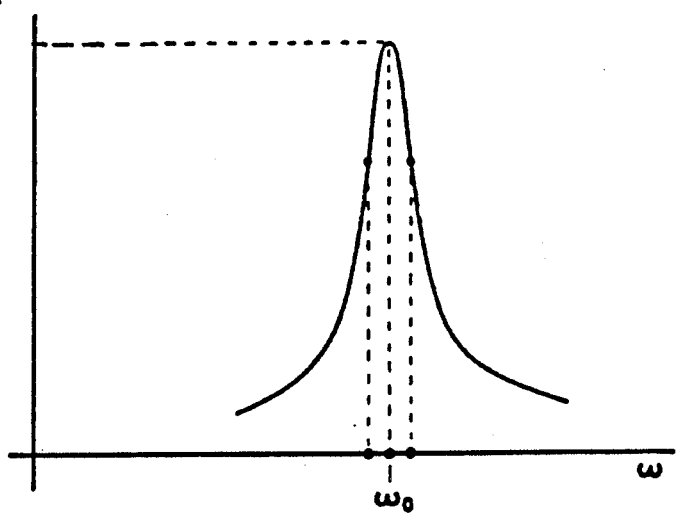
FIG. 7 is a graph showing the amplitude of the central circle frequency of the band pass filter.
Figure 8:
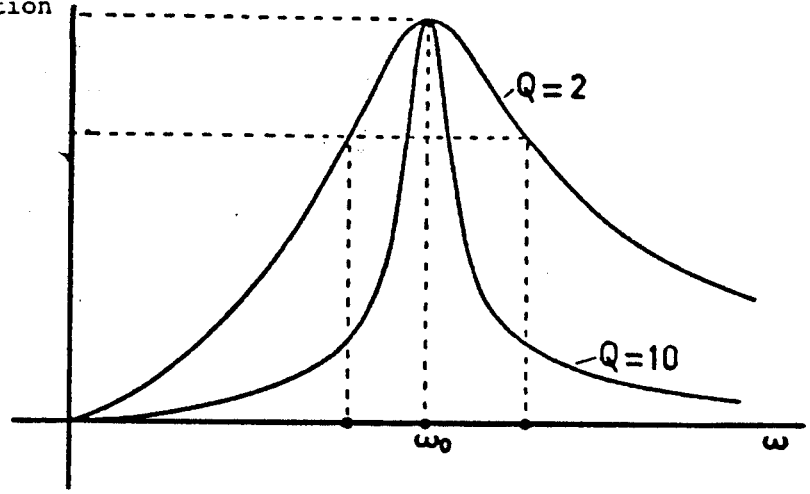
FIG. 8 is a graph showing the measure of selectivity of the band pass filter.

In FIG. 6, 19 indicates one period of the data corresponding with the filtered yarn or stitch frequency graph, 20 the number of periods N proportional to $N_p$, the number of pixels, and 21 one line recording or histogram. The same method applies to the calibration pattern.

The result obtained is then applied via the connection 16 to the read-out unit 8 of a known type, on which the yarn or stitch density then appears in a form permitting the operator of the loom, knitting machine or tenter frame to read out and check the yarn or stitch density.

The result obtained is applied, likewise through the connection 16, to the loom, knitting machine or tenter frame 22 to adjust it for the instantaneous control of the yarn or stitch density, with the result that a product is supplied whose density can be accurately maintained within well defined limits.

In the above manner the yarn or stitch density can be obtained in a very fast and accurate manner with the apparatus described herein, which has a relatively simple construction, so that a continuous and automatic measurement is possible.

The present invention is not intended to be in any way limited to the embodiments described herein, which, without departing from its scope, permit many modifications to be made as regards the form, composition, arrangement and number of parts used for the realization of the invention, among other aspects.

I claim:

1. A method of measuring the yarn density of a woven fabric comprising:

recording a video image of the woven fabric to be examined by means of a video camera, converting the video image by an analog-to-digital converter into digital video data, storing the digital video data in a digital image memory, retrieving and passing the digital image memory data to a central processing unit and converting said data by said central processing unit into the yarn density whereby said converting by said central processing unit comprises converting said digital image memory data by a digital band filter with a central circle frequency $107_o$ which digital band filter is arranged in such a manner that it operates according to the formula:

$$Y_K = A_m \cdot X_{k-m} + A_{m-1} \cdot X_{k-m+1} \cdots + A_o X_k - B_1 \cdot Y_{k-1} - B_2 Y_{k-2} \cdots - B_n Y_{k-n}$$

wherein:

$X_k$ represents a series of points of the digital information characteristic at interspace T before the digital filtering; $Y_k$ represents the said series of points k of the filtered digital information characteristic via digital filtering at the same interspace T; the coefficients A and B are a function of the quality Q, the central circle frequency $\omega_o$ and the interspace T, the converting by said digital band filter being followed by a computation proper of the yarn density from the data converted by said filter.

2. The method of claim 1, in which the central circle frequency $\omega_o$ of the band filter is adjustable as a function of the yarn density of the fabric to be examined.

3. The method of claim 1, in which before conversion of the digital video data, this data is enhanced.

4. The method of claim 3, wherein the enhancement of the digital video data includes at least one of the following steps: contrast expansion, elimination of redundant data from the digital video data and accentuation of relevant data in the digital video data.

5. The method of claim 1, in which converting by a central processing unit comprises deriving a yarn frequency graph from said digital video data, the filter converting the digital image memory data corresponding to said yarn frequency graph.

6. The method of claim 5, wherein the yarn frequency graph is computed by isolating one line from the digital video data.

7. The method of claim 5, wherein the data corresponding with the yarn frequency graph is determined by the computation of a row or column histogram from the digital image data.

8. The method of claim 1, wherein the yarn density is computed, by computing the average of the filtered data corresponding with the yarn frequency graph, subtracting said average from said filtered data, counting the number of whole periods N in the filtered data, counting the number of measuring points $N_p$ in said N periods, and resolving the equation: density$=N/(N_p \times s)$, in which s is a scale factor.

9. An apparatus for measuring the yarn density of a woven fabric, which comprises:
a video camera for recording an analog video image of the woven fabric to be examined,
an analog-to-digital converter for converting the analog video image into digital video data,
an image memory for storing the digital video data, and
a processing unit for converting the digital video data into the yarn density, said processing unit comprising a digital filter with central circle frequency $\omega_o$ and operating according the formula:
$$Y_k = A_m \cdot X_{k-m} + A_{m-\cdot} \cdot X_{k-m+\cdots}$$
$$+ A_o X_k - B_1 \cdot Y_{k-1} - B_2 Y_{k-2} \cdots - B_n Y_{k-}$$
wherein:
$X_k$ represents a series of points of the digital data characteristic at interspace T before the digital filtering; $Y_k$ represents the said series of points k of the filtered digital data characteristic via digital filtering at the same interspace T; the coefficients A and B are a function of the quality Q; the central circle frequency $\omega_o$ and the interspace T, and a computer unit for the computation proper of the yarn density from the data converted by said filter.

10. An apparatus as claimed in claim 9, which further comprises a suitable display unit.

11. The apparatus as claimed in claim 9, in which said processing unit comprises means for calculating a yarn frequency graph.

12. The apparatus of claim 11, in which the means for deriving a yarn frequency graph comprise means for isolating one line from the digital video data.

13. The apparatus of claim 11, in which the means for deriving a yarn frequency graph comprise means for computing a row or column histogram from the digital image data.

14. The apparatus of claim 9, in which the central circle frequency $\omega_o$ of the digital band filter is adjustable in function of the yarn density of the woven fabric to be examined.

15. The apparatus of claim 9, comprising an image enhancing unit for enhancing the digital video data, which comprises at least one of the following devices: a device for contrast expansion, a device for elimination of redundant information from the digital video data and a device for accentuation of relevant data in the digital video data.

16. A method of measuring the stitch density of a knitted fabric comprising:
recording a video image of the knitted fabric to be examined by means of a video camera, converting the video image by an analog-to-digital converter into digital video data, storing the digital video data in a digital image memory, retrieving and passing the digital image memory data to a central processing unit and converting said data by said central processing unit into the stitch density, whereby said converting by said central processing unit comprises converting said digital image memory data by a digital band filter with central circle frequency $\omega_0$, which digital band filter is arranged in such a manner that it oeprates according to the formula:
$$Y_K = A_m \cdot K_{k-m} + A_{m-1} \cdot X_{k-m+1} \cdots$$
$$+ A_o X_k - V_1 \cdot H_{k-1} - B_2 Y_{k-2} \cdots - B_n Y_{k-n}$$
wherein: $X_k$ represents a series of points of the digital data characteristic at interspace T before the digital filtering; $Y_k$ represents the said series of points k of the filtered digital data characteristic via digital filtering at the same interspace T; the coefficients A and B are a function of the quality Q, the central circle frquency $\omega_o$ and the interspace T, the converting by said digital band filter being followed by a computation proper of the stitch density from the data converted by said filter.

17. The method of claim 16, in which the central circle frequency $\omega_o$ of the band filter is adjustable as a function of the stitch density of the fabric to be examined.

18. The method of claim 16, in which before conversion of the digital video data, this data is enhanced.

19. The method of claim 16, in which the enhancement of the digital video data includes at least one of the following steps: contrast expansion, elimination of redundant data from the digital video data and accentuation of relevant data in the digital video data.

20. The method of claim 16, in which converting by a central processing unit comprises deriving a stitch frequency graph from said digital video data, the filtering converting the digital image memory data corresponding to said stitch frequency graph.

21. The method of claim 20, in which the stitch frequency graph is computed by isolating one line from the digital video data.

22. The method of claim 20, in which the data corresponding with the stitch frequency graph is determined by the computation of a row or column histogram from the digital image data.

23. The method of claim 16, in which the stitch density is computed by computing the average of the filtered data corresponding with the stitch frequency graph, subtracting said average from said filtered data, counting the number of whole periods N in the filtered data, counting the number of measuring points $N_p$ in said N periods, and resolving the equation:

density$=N/(N_p \times s)$, in which s is a scale factor.

24. An apparatus for measuring the stitch density of a knitted fabric, which comprises:
a video camera for recording an analog video image of the knitted fabric to be examined,
an analog-to-digital converter for converting the analog video image into digital video data, an image memory for storing the digital video data, and a processing unit for converting the digital video data into the stitch density, said processing unit comprising a digital band filter with central circle frequency $\omega_o$ and operating according to the formula:

$$Y_k A_m \cdot X_{k-m} + A_{m-1} \cdot X_{k-m+1} \cdots + A_o X_k - B_1 \cdot Y_{k-1} - B_2 Y_{k-2} \cdots - B_n Y_{k-n}$$

wherein:

$X_k$ represents a series of points of the digital data characteristic at interspace T before the digital filtering; $Y_k$ represents the said series of points k of the filtered digital data characteristic via digital filtering at the same interspace T; the coefficients A and B are a function of the quality Q, the central circle frequency $\omega_o$ and the interspace T, and a computer unit for the computation proper of the stitch density from the filtered data converted by said filter.

25. The apparatus as claimed in claim 24, which further comprises a suitable display unit.

26. The apparatus of claim 24, in which said processing unit comprises means for calculating a stitch frequency graph.

27. The apparatus of claim 26, in which the means for deriving a stitch frequency graph comprise means for isolating one line from the digital video data.

28. The apparatus of claim 26, in which the means for deriving a stitch frequency graph comprise means for computing a row or column histogram from the digital image data.

29. The apparatus of claim 24, in which the central circle frequency $\omega_o$ of the digital band filter is adjustable in junction of the stitch density of the knitted fabric to be examined.

30. The apparatus of claim 24, which comprises an image enhancing unit for enhancing the digital video data, which comprises at least one of the following devices: a device for contrast expansion, a device for elimination of redundant data from the digital video data and a device for accentuation of relevant data in the digital video data.

* * * * *

UNITED STATES PATENT AND TRADEMARK OFFICE
CERTIFICATE OF CORRECTION

PATENT NO. : 4,953,400

DATED : September 4, 1990

INVENTOR(S) : Filip O.P. BOSSUYT

It is certified that error appears in the above-identified patent and that said Letters Patent is hereby corrected as shown below:

Column 2, lines 43-50, the passage "The suffix o ... All" should appear instead at Column 2, line 15, after "filter."

Column 2, lines 4 and 5, the equation should read:

$$-- Y_k = A_m \cdot X_{k-m} + A_{m-1} \cdot X_{k-m+1} \cdots + A_o X_k - B_1 \cdot Y_{k-1} - B_2 Y_{k-2} \cdots - B_n Y_{k-n} --$$

Column 5, lines 25-30, the equations should read:

$$-- Y_k + B_1 \cdot Y_{k-1} + B_2 \cdot Y_{k-2} \cdots + B_n \cdot Y_{k-n} = A_m \cdot X_{k-m} + A_{m-1} \cdot X_{k-m+1} \cdots + A_o \cdot X_k$$

or $$Y_k = A_m \cdot X_{k-m} + A_{m-1} \cdot X_{k-m+1} \cdots + A_o \cdot X_k - B_1 \cdot Y_{k-1} - B_2 \cdot Y_{k-2} \cdots - B_n \cdot Y_{k-n} --$$

UNITED STATES PATENT AND TRADEMARK OFFICE
CERTIFICATE OF CORRECTION

PATENT NO. : 4,953,400
DATED : September 4, 1990
INVENTOR(S) : Filip O.P. BOSSUYT It is certified that error appears in the above-identified patent and that said Letters Patent is hereby corrected as shown below:

Column 5, lines 39-41, the equations should read:

$$--Y_k+B_1 \cdot Y_{k-1}+B_2 \cdot Y_{k-2}=A_o \cdot X_k+A_1 \cdot X_{k-1}+A_2 \cdot X_{k-2}$$

or $$Y_k=A_2 \cdot X_{k-2}+A_1 \cdot X_{k-1}+A_o \cdot X_k-B_1 \cdot Y_{k-1}-B_2 \cdot Y_{k-2} \;--$$

Column 9, lines 33 and 34;
Column 10, lines 17 and 18; and
Column 11, lines 9 and 10 the equation should read:

$$--Y_k = A_m \cdot X_{k-m}+A_{m-1} \cdot X_{k-m+1}\cdots\cdots$$
$$+ A_o\, X_k - B_1 \cdot Y_{k-1}-B_2 Y_{k-2}\cdots-B_n Y_{k-n} \;--$$

Signed and Sealed this

Twenty-eighth Day of April, 1992

*Attest:*

HARRY F. MANBECK, JR.

*Attesting Officer*      *Commissioner of Patents and Trademarks*